(12) United States Patent
Salmi et al.

(10) Patent No.: US 9,453,792 B2
(45) Date of Patent: Sep. 27, 2016

(54) DEVICE, SYSTEM AND METHOD FOR MEASURING MOISTURE OF STRUCTURE MATERIAL

(75) Inventors: Risto-Matti Salmi, Tampere (FI); Toni Luopajarvi, Tampere (FI)

(73) Assignee: WIISTE OY, Tampere (FI)

( * ) Notice: Subject to any disclaimer, the term of this patent is extended or adjusted under 35 U.S.C. 154(b) by 235 days.

(21) Appl. No.: 14/342,065

(22) PCT Filed: Aug. 30, 2012

(86) PCT No.: PCT/FI2012/000035
§ 371 (c)(1),
(2), (4) Date: Feb. 28, 2014

(87) PCT Pub. No.: WO2013/030430
PCT Pub. Date: Mar. 7, 2013

(65) Prior Publication Data
US 2014/0216143 A1   Aug. 7, 2014

(30) Foreign Application Priority Data
Aug. 30, 2011  (FI) .................................... 20115846

(51) Int. Cl.
G01N 19/10 (2006.01)
G01N 33/38 (2006.01)
G01N 27/04 (2006.01)
G01N 27/22 (2006.01)

(52) U.S. Cl.
CPC ............ *G01N 19/10* (2013.01); *G01N 33/383* (2013.01); *G01N 27/048* (2013.01); *G01N 27/223* (2013.01)

(58) Field of Classification Search
None
See application file for complete search history.

(56) References Cited

U.S. PATENT DOCUMENTS

| 4,929,885 A * | 5/1990 | Dishman | G01N 33/246 324/664 |
| 5,730,024 A * | 3/1998 | Sahlen | G01N 33/383 324/694 |
| 7,658,096 B2 * | 2/2010 | Pinto | G01D 11/245 73/29.05 |
| 2006/0272392 A1 | 12/2006 | Kanare | |
| 2009/0100926 A1 | 4/2009 | Kanare et al. | |
| 2010/0308980 A1 * | 12/2010 | Gosset | G08C 19/12 340/286.02 |

FOREIGN PATENT DOCUMENTS

| DE | 4427244 | 2/1996 |
| JP | 20050078473 A | 3/2005 |
| WO | 9964856 A1 | 12/1999 |
| WO | 2007139533 A1 | 12/2007 |
| WO | 2009-092771 | 7/2009 |

OTHER PUBLICATIONS

International Search Report, dated Dec. 20, 2012, from corresponding PCT application.

* cited by examiner

*Primary Examiner* — Hezron E Williams
*Assistant Examiner* — Mark A Shabman
(74) *Attorney, Agent, or Firm* — Young & Thompson

(57) ABSTRACT

The invention relates to a device, system and method for measuring moisture in building structures. A tubular body part (100) may be embedded in a material during its casting. Hole(s) (106) provided in the body part (100) lets moisture inside a space separated by the body part (100). Measuring element including electronics (102) and a sensor (104) functionally connected to the body part (100) is used to measure the separated space 108. With a reading device (234), the results may then be read from above surface due to a provided wireless link between the measuring element (102) and (104) and the reading device (234).

16 Claims, 6 Drawing Sheets

Figure 1:
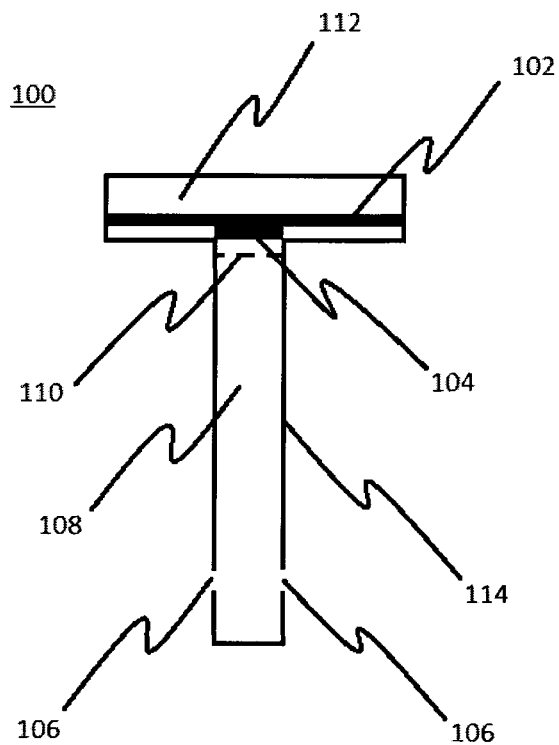

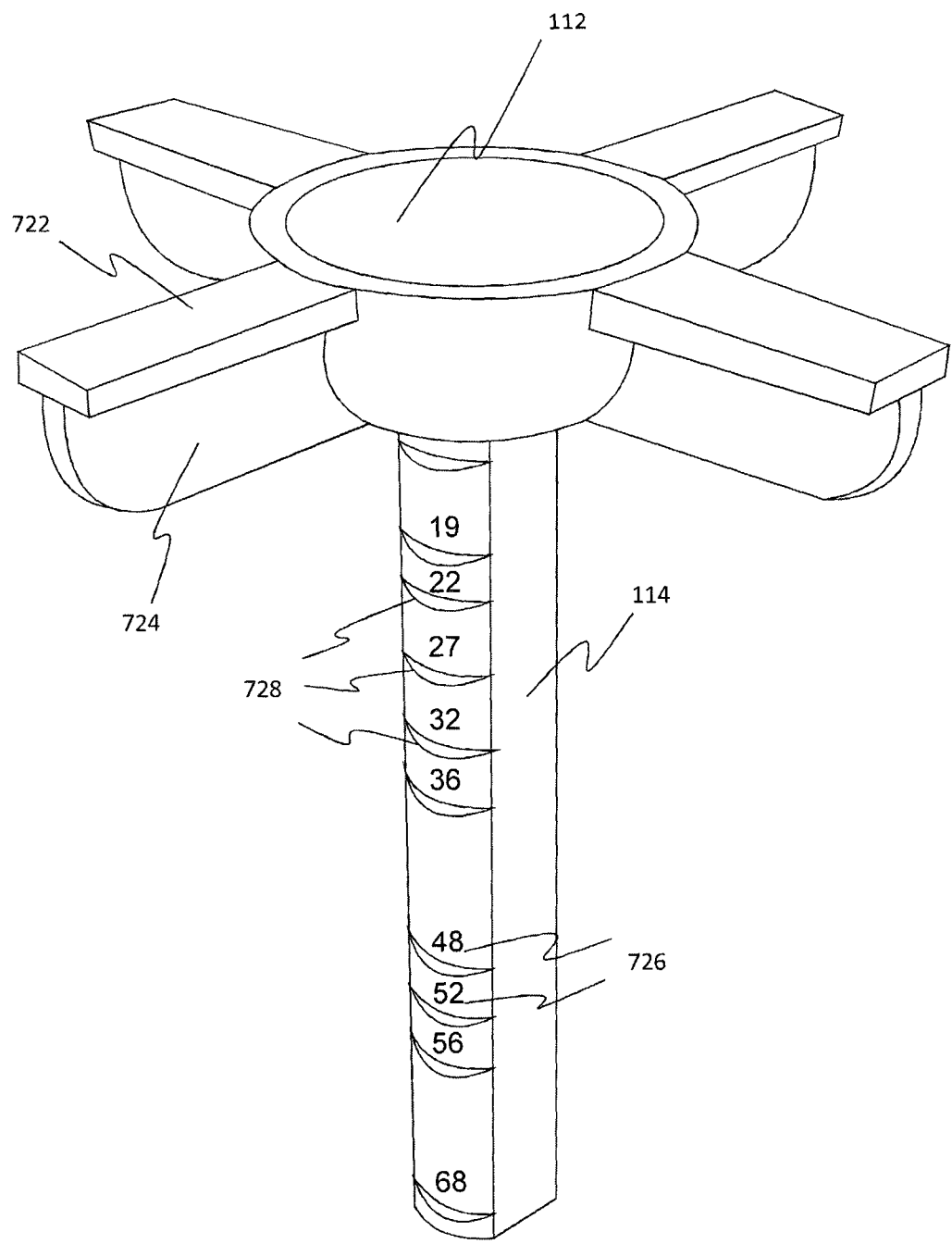
FIG. 9
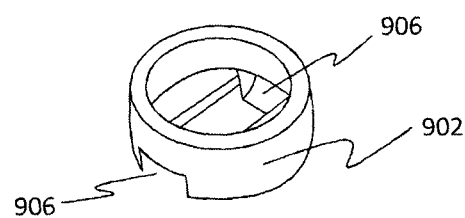

DEVICE, SYSTEM AND METHOD FOR MEASURING MOISTURE OF STRUCTURE MATERIAL

TECHNICAL FIELD

The invention relates generally to a device, system and method for measuring moisture. More specifically the invention relates to an embeddable device with wireless communication, a system comprising said embeddable device configured to connect with a reading device and a method for measuring moisture from inner structures of a building.

BACKGROUND TECHNOLOGY

Measuring moisture content in building structures during the construction is important. If the structure material, e.g. concrete, is being coated too early it may cause severe structural damages in the future. Having moisture in structure material for a longer period may cause growth of mold, which can adverse effects to health. Moisture also destroys the material in time causing it to decay. The financial cost repairing these damages may rise to large numbers.

On the other hand, letting the structure material dry for an unnecessary long time causes delays in construction work which also lead to extra financial costs.

It is also important to keep track on the moisture content of structures during the usage in order to detect possible water damages.

There are some prior known solutions for measuring moisture in building structures. However these inventions and methods have some limitations. In one known method a hole is drilled in the material desired to be measured, then the hole is cleaned and a sensor, measuring relative humidity, is mounted in the hole.

In another prior known method material samples are taken from a desired depth either by drilling or chipping. The samples are then sealed in a testing tube with a relative humidity measuring sensor. The moisture from the sample mixes with the air inside the tube and after a while the moisture has spread out in the space inside the tube and the humidity of the space becomes stable. The result is then read with a reading device.

The known methods are time-consuming and susceptible to errors due to the multiple preparation steps before reading the results. The user's competence to perform the measurement plays also a part in the reliability of the final result. In addition, the methods are not suitable for tracking moisture during the usage of the building due to the necessity of breaking the structural surface. Additionally, it may take a long time, such as 8 hours, until the humidity of the measurement space becomes stable, and therefore the measurement procedure may be slow.

SUMMARY OF THE INVENTION

The purpose of the present invention is to avoid or reduce the above disadvantages of the prior art. Especially the present invention tries to solve the problem how to measure the moisture content of a material in a reliable and feasible manner from various depths without breaking the surface of the material.

According to one aspect of the present invention a device for measuring moisture in structure materials is characterized in that the device comprises:

a body part for separating a space in the material to be measured, said body part comprising at least one hole or opening or the like for moisture to passage through inside the separated space, and measuring means comprising a sensor for measuring humidity and/or temperature in said separated space and electronics for transferring data wirelessly between the measuring means and a reading device and said electronics for receiving operating energy wirelessly from the reading device, wherein said body part is embedded in the material to be measured during casting, said measuring means being functionally connected to the body part, said data transfer and receiving of operating energy being provided in a non-invasive manner.

According to another aspect of the present invention a measuring system for measuring moisture in structure materials is characterized in that the system comprises a measuring device according to the invention, and a reading device for receiving and collecting the results measured and transmitted by the measuring means of the measuring device.

According to a further aspect of the invention a method for measuring moisture inside a structure is characterized in that a moisture measuring device according to the invention is embedded in the material to be measured during casting of the material, moisture is measured with the measuring device, and measuring results are transferred to a reading device, said measuring process being provided without breaking the surface of the material Some preferable embodiments of the invention are described in the dependent claims.

In one embodiment the material to be measured is concrete.

In another embodiment the connection between the measuring means and the reading device is provided through a wireless link. The wireless link may be provided through any known solution suitable for the purpose, wherein the wireless range is strong enough to transfer data from the measuring means to the reading device. The measuring means and reading device may in some embodiments be separated by insulation material and/or coating. The wireless link may be e.g. an inductive link, a radio link and/or ultrasound. If the measuring device remains visible, it may also be possible to use optical radiation for the data transfer.

In another embodiment the sensor and electronics may be protected with a filter through which vapor is penetrated.

In another embodiment the sensor may be placed in the upper end of the body part, together with the electronics of the measuring means. This way the sensor and other electronics can be produced into a compact module. The sensor may, instead, also be provided adjacent the hole(s).

Yet, in another embodiment the sensor is provided within air inside of the body part. The sensor may also be attached or embedded in the frame of the body part. In some embodiments of the present invention the space and/or the hole and/or the filter may be replaced with wood, clay or some other suitable moisture transferring material.

The embeddable tube of the present invention may be plastic, aluminum, silicone or some other material suitable for the purpose.

In one embodiment of the present invention said hole is on the side of said body part. Said hole may also be in the bottom of said body part. In another embodiment the whole bottom of the body part is an opening. In some embodiments there are multiple holes on different heights of the body part with a purpose of measuring average moisture content in the material within a height range.

In one embodiment of the present invention the body part is embedded in the material during its casting. The connection between the reading device and the measuring means is provided without breaking the surface of the material to be measured. It is also possible to provide the measurements after coating of the structure without breaking the coating.

In another embodiment the body part is configured with guiding wings for keeping the measuring device straight and in line with the surface. The guiding wings may be, preferably, provided in the upper part of the embodiment for attaining maximum benefit of their purpose. The wings may also be penetrated with different attaching means e.g. screws and/or nails for fastening of the measuring device. The wings may also have prefabricated slots for said fastening purpose.

In a further embodiment the body part is configured with prefabricated cuts along the surface, which cuts provide assistance when cutting of said body part. The cuts may be utilized when a measurement is wanted from a certain depth. The measuring device may be, optionally, provided with a perforated end plug.

Significant advantages can be achieved with the present invention when compared to the prior known solutions. With the moisture measuring device according to the present invention it is possible to measure the moisture content from any depths. Besides, the measuring is provided in a way that the reliability of the measurement is not affected by the competence of the user in providing a suitable measurement space, for example.

With the term "measuring means" in this application is referred to a sensor and electronics functionally connected to each other making it possible to measure and transfer data to a reading device.

SHORT DESCRIPTION OF THE DRAWINGS

Figure 2:
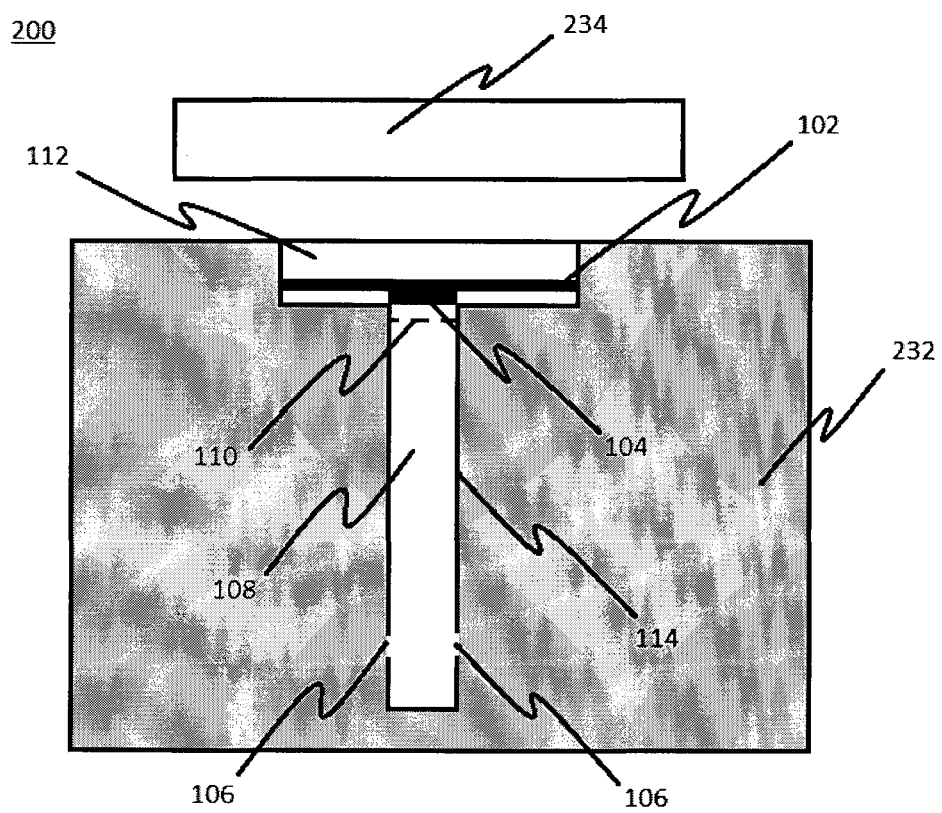
Figure 3:
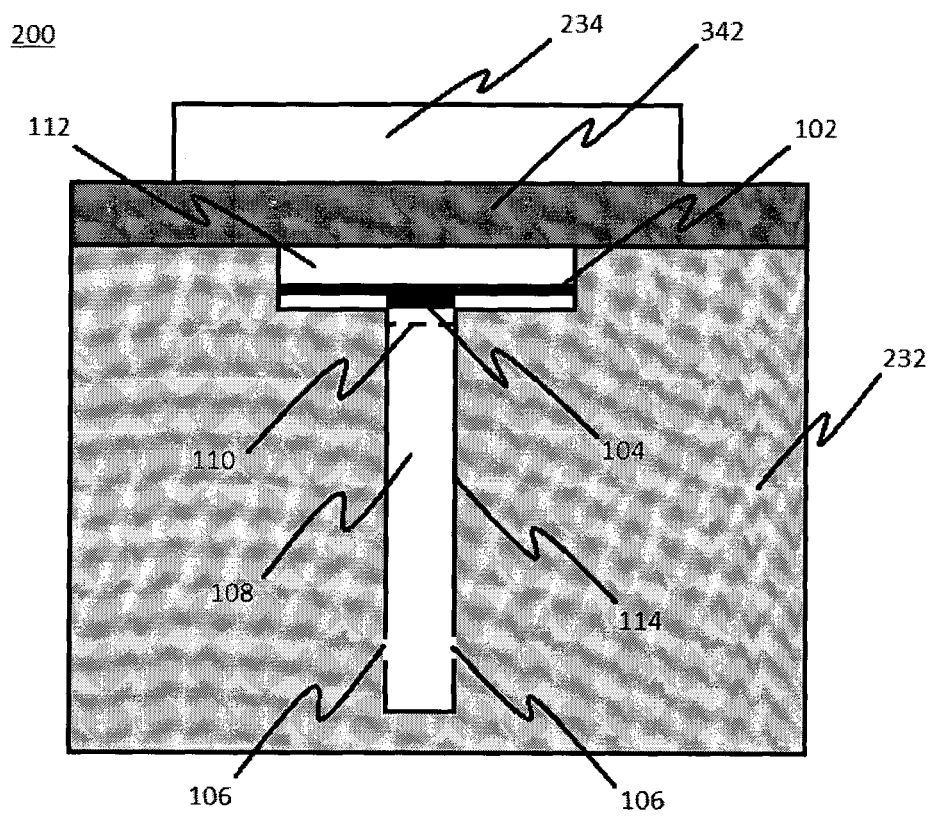
Figure 4:
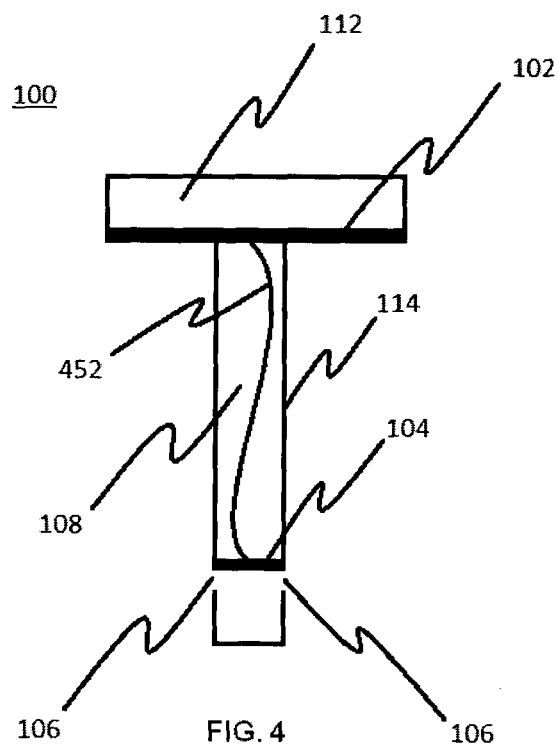
Figure 5:
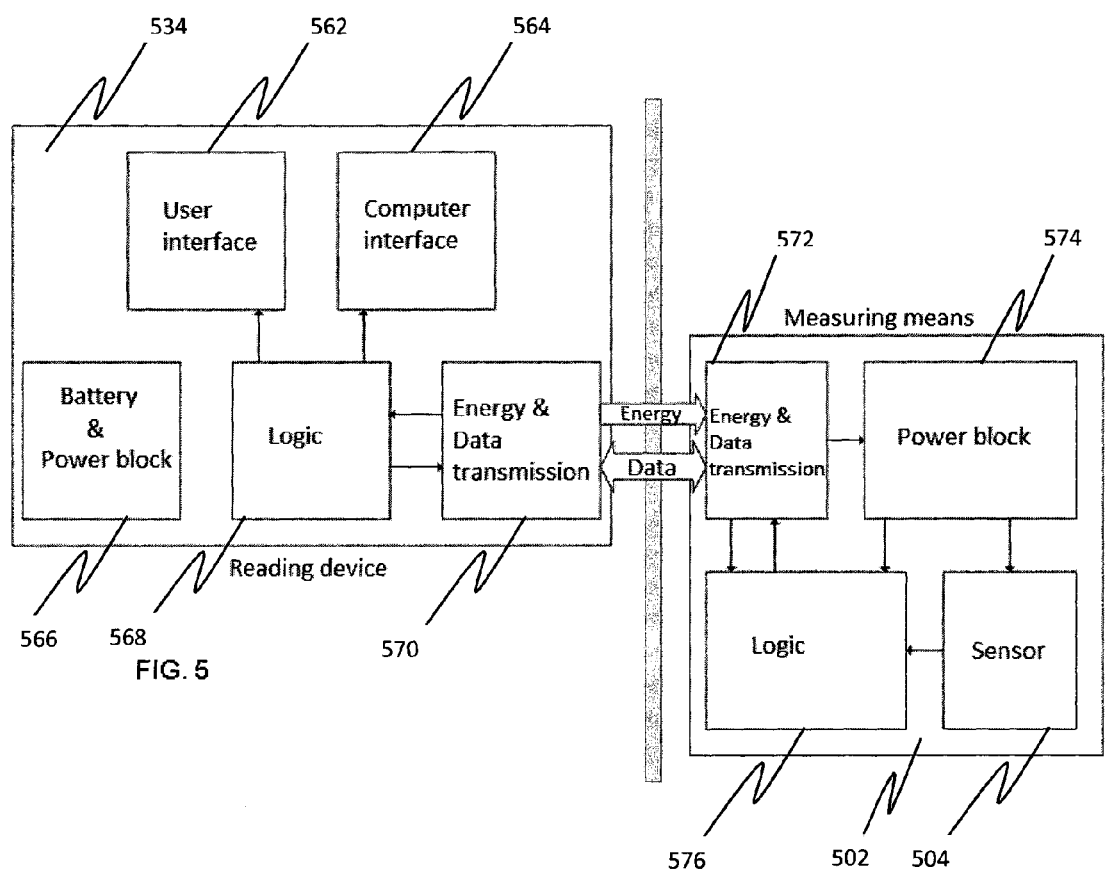
Figure 6:
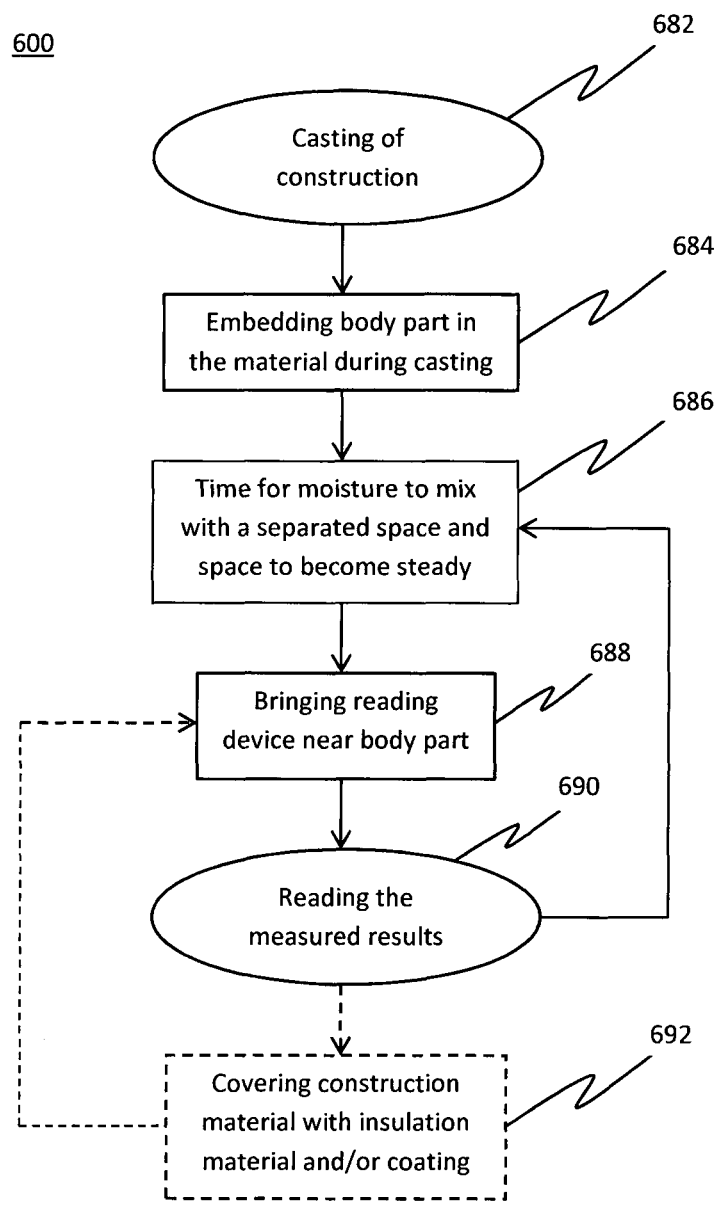
Figure 7:
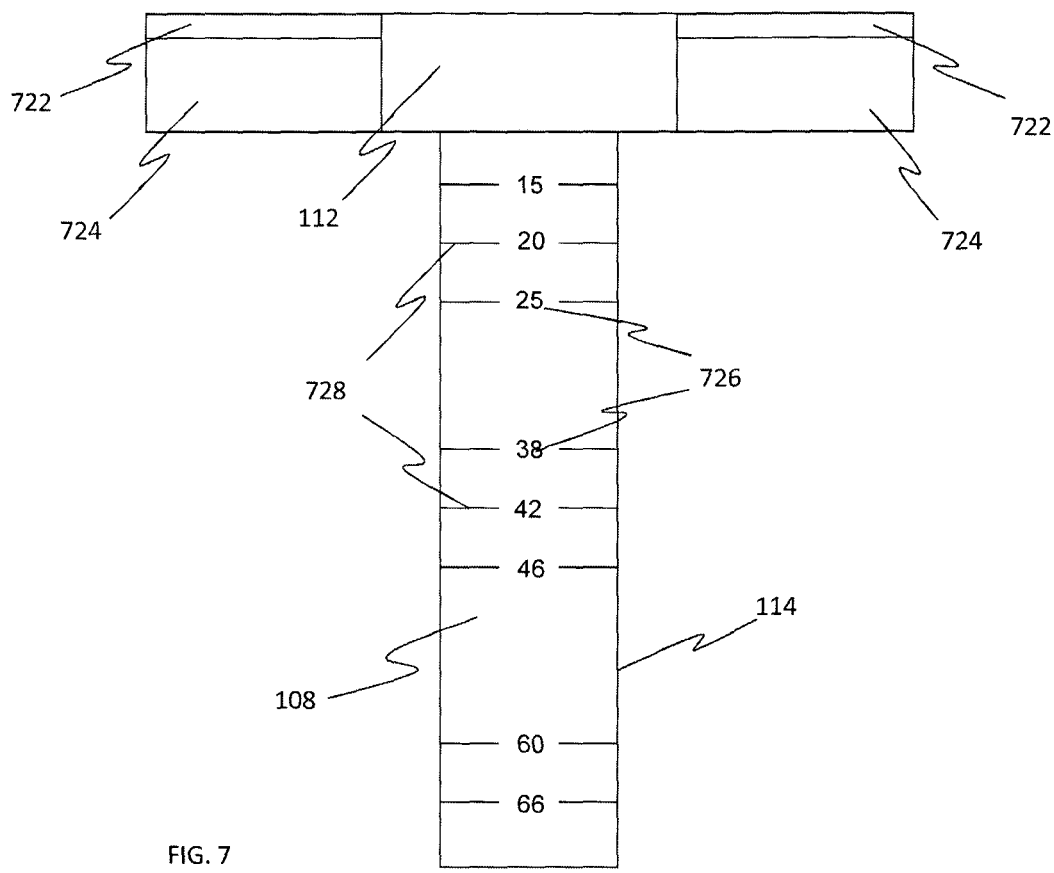
Figure 8:
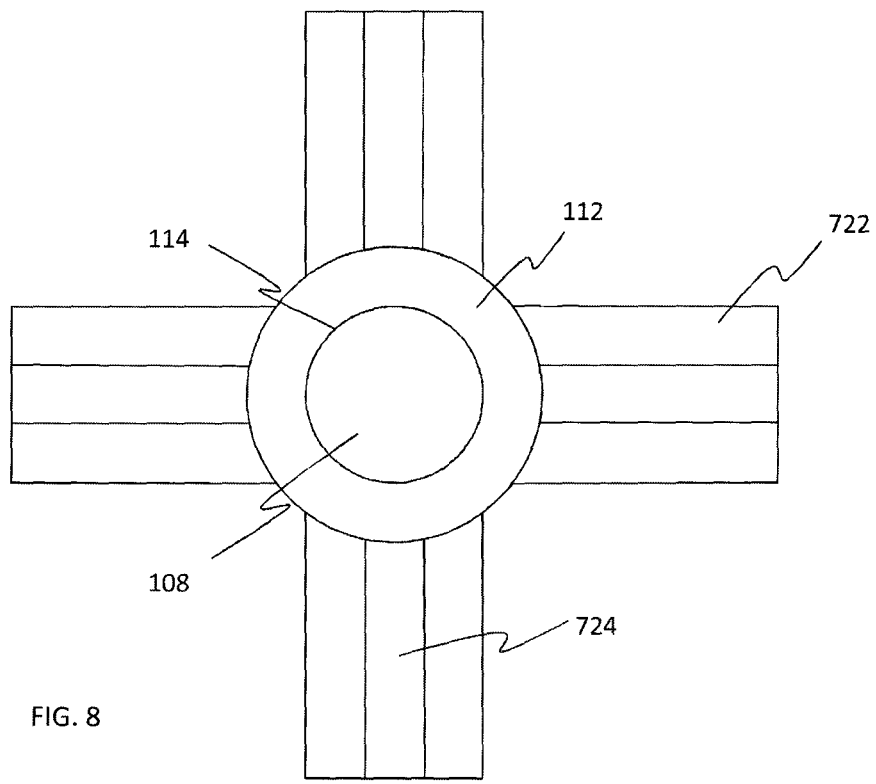

Next, the invention is described in more detail with reference to the appended drawings, in which FIG. 1 illustrates a side view of a body part and measuring means according to an embodiment of the present invention, FIG. 2 illustrates a side view of a moisture measuring apparatus during construction according to an embodiment of the present invention, FIG. 3 illustrates a side view of a moisture measuring apparatus when the body part has been covered according to an embodiment of the present invention, FIG. 4 illustrates a side view of a body part and measuring means according to an embodiment of the present invention, where the sensor is provided adjacent the hole(s), FIG. 5 illustrates a block diagram of a system according to an embodiment of the present invention, FIG. 6 illustrates a flow diagram of an exemplary method of the invention, FIG. 7 illustrates a side view of a body part according to an embodiment of the present invention, where the body part is configured with guiding wings and prefabricated cuts, FIG. 8 illustrates a bottom view of a body part according to an embodiment of the present invention, where the body part is configured with guiding wings and FIG. 9 illustrates an axonometric view of a body part according to an embodiment of the present invention, where the body part is configured with guiding wings, prefabricated cuts and an end plug.

DETAILED DESCRIPTION OF THE EMBODIMENTS

FIG. 1 illustrates a side view of a body part and measuring means according to an embodiment of the present invention.

The body part 100 of the present invention comprises an embeddable tube 114 separating a space 108 and at least one hole 106 or opening or the like. An upper part 112 of the body part 100 is provided such that data and energy transferring electronics 102 for e.g. data and energy transfer fits inside. A sensor 104 is connected with the electronics 102 and located in such a way that it can measure the moisture content in the separated space 108. A water vapor penetrating filter 110 may be placed to protect the sensor 104 and the electronics 102 from extraneous substances such as dirt.

The size and shape of the body part 100 of the present invention can be of any size and shape suitable for the purpose. The optimal size and shape of the body part depends on the thickness of the material to be measured and from which depths the measurements are to be made. As an example, the measuring device may be shaped so that when the top of the device is aligned with the surface of the material to be measured, the opening to the measurement space locates at the suitable measurement depth according to any specific requirement. As an example, if the structure can dry through one surface only, the measurement depth may be e.g. 40% of the structure thickness from the surface.

Making the tubular part 114 wider, and thus expanding the volume of the separated space 108, may affect the measuring time. The larger the volume the longer it takes for the moisture penetrating into the separated space 108, to even out and become in balance with the moisture content in the material to be measured. The material used in the body part 100 may be any material suitable for the purpose, e.g. plastic such as epoxy, metal such as aluminum, rubber, silicone, glass and/or porcelain. It is obvious to a person skilled in the art that these materials may be used separately or they may be combined in a favorable way. The body part 100 is preferably embedded in the material to be measured during its casting.

The separated space 108 in the present invention has to be filled with medium conveying moisture. A conventional solution is to fill the space 108 with air, but air may also be replaced with some other medium or material conveying moisture i.e. wood and/or clay.

One essential part of the present invention is that moisture must be able to penetrate the body part 100 into the separated space 108. This is achieved by providing at least one hole 106 or opening or the like in the body part 100. The hole(s) may be of any shape and size and be placed anywhere on the tubular part 114 of the body part. The amount of holes 106 may also vary. By placing the hole 106 on a selected height of the tubular part 114 it is possible to measure at a desired depth in the material. In one embodiment of the present invention multiple holes 106 are provided on different heights with the intention of getting average moisture content. In another embodiment the whole bottom of the body part 100 is an opening. To a person skilled in the art it is obvious how to place the hole(s) in a favorable way according to the measurement need. In some embodiment of the present invention the hole(s) may be replaced with moisture conveying material such as wood and/or clay.

In one embodiment of the present invention a vapor penetrating filter 110 or a protective sheet or the like is provided to protect the sensor 104 and electronics 102 from extraneous substances such as dirt. The filter 110 may be i.e. PET-foam, wood, clay or some other material that transmit vapor and is suitable for the purpose. In another embodiment the filter 110 is left out.

FIG. 2 illustrates a side view of a moisture measuring system 200 according to an embodiment of the present invention. The moisture measuring apparatus 200 comprises a body part 100, measuring means (electronics 102 and a sensor 104) and a reading device 234. This figure illustrates the usage of the measuring apparatus during construction. The moisture measuring apparatus may be embedded in a material 232 to be measured during its casting. The upper part 112 is provided in the same level with the surface of the material 232. The measured data may be transferred to a reading device 234 through a provided wireless link.

The electronics 102 in the present invention may be implemented in various ways. The purpose of the electronics 102 is to transfer data from a sensor 104 to a reading device 234. The electronics may be provided with energy from the reading device in a wireless manner, such as inductive energy transfer. In one embodiment the electronics is provided on a conventional circuit board. The electronics may also be covered with epoxy. In one embodiment of the invention the electronics is provided directly in the epoxy, without a circuit board. In another embodiment the electronics may be split on multiple circuit boards. In a further embodiment certain parts of the electronics may be on the circuit board and some parts may be separate without circuit board.

FIG. 3 illustrates a side view of a moisture measuring apparatus 200 according to an embodiment of the present invention. The figure illustrates the measuring process when the structure/building is already in normal use. The body part 100 and the measuring means 104 and 102 have been covered with insulation material and/or coating 342. Due to the wireless link the data from the measuring means can still be transferred to the reading device 234. Because the electronics 102 is provided near the surface, the distance to the reading device 234 remains within the operating range.

According to a preferable embodiment of the present invention the sensor 104 is an integrated RH&T-sensor, measuring both relative humidity and temperature. In another embodiment these two features may be separated into two sensors. The relative humidity sensor may be based on i.e. capacitance, resistance or optics. Other solutions suitable for the purpose may also be implemented. In some embodiment of the present invention the sensor 104 is embedded in the frame of the body part. In another embodiment the sensor may be placed adjacent the hole(s), which is illustrated in FIG. 4. When sensor 104 is placed adjacent hole(s), an electrical cable 452 connects the sensor 104 and the electronics 102 with each other.

FIG. 5 illustrates a functional block diagram of an exemplary system 500 according to the invention. According to an embodiment of the present invention the reading device 534 has a user interface 562 which is manually operated in a conventional manner. The reading device 534 preferably acts mainly as the user interface of the measuring apparatus, but it may also provide processing of the received measurement results by, for example, converting the result into dew point value. In some embodiment the reading device has an interface 564 for connecting a computer for storing measured data. The reading device has also an own power source 566, which may be chargeable.

The actual measurement takes place in the measuring means 502 using the sensor 504. Data is then transferred to the reading device 534. In a preferable embodiment of the present invention energy and data may be transferred between the measuring means 502 and the reading device 534 through a wireless inductive link, provided with the energy and data transmissions 570 and 572. The transmission frequency may preferably be in the range 20 kHz-20 GHz and more preferably in the range 20 kHz-20 MHz. The wireless link may also be a radio link or ultrasound. Also optical radiation may be used if the measuring means remains visible at the surface of the structure. The measuring means has a power block 574, which receives power from the reading device. In one embodiment the measuring means 502 are provided with an own power source i.e. battery, which power source may be charged through a wireless link. In another embodiment a power source, such as battery, in the measuring means 502 is not charged and only data is transferred between the measuring means 502 and the reading device 534. In embodiments where the measuring means 502 have an own power source an alarm set may be included in the measuring means 502 with the aim of e.g. alerting when the material has dried enough. After the material has dried and the structure is being used, the alarm set may alert if the moisture content of the material becomes too high, which possibly means an occurrence of water damages. Logic functions of both devices are provided by logic circuits 568 and 576.

FIG. 6 illustrates a flow diagram of an exemplary method 600 according to the present invention. First a construction material 232 is poured, step 682. The body part 100 of the present invention is embedded in the material 232 during casting in step 684. The moisture in the material 232 mixes with the separated space 108, step 686. When the space 108 becomes in a stable state the reading device 204 may be brought near the body part 100, step 688, for reading the measured results in step 690. The measurements may be repeated as required. If it is planned to cover the material with insulation material and/or coating 302, the material 232 needs to be dry enough before covering. After it is covered in step 692 the measuring may be repeated e.g. for inspections of water damages.

The present invention can also be used for measuring a structure where the material has already been hardened. In such a case a cavity is drilled in the hardened material, in which the body part 100 may be embedded together with filling compound. The results may be read with a reading device 234 in the same way as presented earlier in the text.

In FIGS. 7, 8 and 9 illustrate embodiments of the body part 100 of the present invention. The body part is configured with guiding wings comprising of horizontal 722 and vertical 724 sections. The guiding wings 722 and 724 are provided adjacent the upper part 112 and keeps the body part straight and in line with the surface when embedded in a material to be measured. The guiding wings 722 and 724 may also be penetrated with different attaching means e.g. screws and/or nails for fastening of the measuring device. The measuring device can be fastened to the casting mold, base, insulation material or concrete slab, for example. The wings may also have prefabricated slots for said fastening purpose. Fastening of the measuring device by utilizing the guiding wings 722 and/or 724 is especially advantageous when measurements are needed to be taken from other than downwards embeddable places, such as floors, e.g. ceilings and walls.

In FIGS. 7 and 9 are also illustrated embodiments of the body part 100 configured with prefabricated cuts 728. Near the cuts 728 may also be preprinted dimensions 726 representing a preferred measurement depth. FIG. 9 also shows an optional end plug 902 with hole(s) 906, which end plug 902 may be attached to the end of the tubular part 114 for protecting the inner parts of the measuring device 100 from penetrating material, when embedding the device in the material to be measured. The prefabricated cuts 728 along with the preprinted dimensions 726 will ease the measurement from a desired depth. When the user wants to get a measurement result from a desired depth, he/she simply breaks the tubular part 114 along a prefabricated cut 728 with the corresponding dimension 726 and embeds the measuring device 100 in the material to be measured.

It should be also noted that although the device is embedded in a horizontal structure in the above embodiments, it is naturally possible to use the invention also for structures in other orientations, such as vertical structures. In such case the embedded device has a corresponding orientation relative to the surface of the structure. The scope of the invention is determined by the attached claims together with the equivalents thereof. The skilled persons will again appreciate the fact that the explicitly disclosed embodiments were constructed for illustrative purposes only, and the scope will cover further embodiments, embodiment combinations and equivalents that better suit each particular use case of the invention.

The invention claimed is:

1. A device for measuring moisture in structure materials, comprising:
    a body part for separating a space in the material to be measured, said body part comprising at least one hole or opening for moisture to passage through inside the separated space, and
    a sensor for measuring humidity and/or temperature in said separated space and electronics for transferring data wirelessly between the sensor and a reading device,
    wherein a distance between the hole or opening and a top surface of the device equals a measuring depth in the material, and said body part is embedded in the material to be measured during casting so that the top surface of the device is on the level of the casting surface, and wherein, said sensor being functionally connected to the body part, said data transfer being provided in a non-invasive manner.

2. The device for measuring moisture according to claim 1, wherein said material is concrete.

3. The device for measuring moisture according to claim 1, comprising electronics for receiving operating energy wirelessly from the reading device in a non-invasive manner.

4. The device for measuring moisture according to claim 1, the device comprising an inductive link for transferring data to a reading device and for receiving operating energy from the reading device.

5. The device for measuring moisture according to claim 1, the device further comprising a radio link for transferring data to a reading device and for receiving operating energy from the reading device.

6. The device for measuring moisture according to claim 1, where said sensor is located near to the measuring means.

7. The device for measuring moisture according to claim 1, where said sensor is located adjacent said hole(s).

8. The device for measuring moisture according to claim 1, where there is air inside the body part.

9. The device for measuring moisture according to claim 1, where said sensor is embedded or attached to the frame of the body part.

10. The device for measuring moisture according to claim 1, where said body part has guiding wings for facilitating embedding.

11. The device for measuring moisture according to claim 1, where said body part has attachment means for attaching the measuring device into a structure.

12. The device for measuring moisture according to claim 1, where said body part prefabricated cuts, for facilitating a desired measurement depth.

13. A measuring system for measuring moisture in structure materials, comprising the device for measuring moisture according to claim 1, and a reading device for receiving and collecting the results measured and transmitted by the sensor.

14. The measuring system according to claim 13, wherein the reading device is configured to provide energy for the measuring device in a wireless, inductive or radio wave, manner.

15. A method for measuring moisture inside a structure, comprising:
    embedding the device for measuring moisture according to claim 1 in the material to be measured during casting of the material, moisture is measured with the device for measuring moisture, and
    transferring measuring results to a reading device, said measuring process being provided without breaking a surface of the material.

16. The method according to claim 15, wherein the measurement device is embedded into the material so that the top surface of the device is aligned on the same level with a surface of the material to be measured.

* * * * *